United States Patent
Ko

(10) Patent No.: US 10,533,993 B2
(45) Date of Patent: Jan. 14, 2020

(54) TEST STRIP, INSPECTION SYSTEM AND INSPECTION METHOD THEREOF

(71) Applicant: Cheng-Hao Ko, Hsinchu County (TW)

(72) Inventor: Cheng-Hao Ko, Hsinchu County (TW)

( * ) Notice: Subject to any disclaimer, the term of this patent is extended or adjusted under 35 U.S.C. 154(b) by 393 days.

(21) Appl. No.: 15/256,638

(22) Filed: Sep. 5, 2016

(65) Prior Publication Data
US 2018/0067105 A1 Mar. 8, 2018

(51) Int. Cl.
| | | |
|---|---|---|
| *G01N 33/52* | (2006.01) | |
| *G01N 21/29* | (2006.01) | |
| *G01N 21/78* | (2006.01) | |
| *G01N 21/27* | (2006.01) | |

(52) U.S. Cl.
CPC ......... *G01N 33/521* (2013.01); *G01N 21/274* (2013.01); *G01N 21/293* (2013.01); *G01N 21/78* (2013.01)

(58) Field of Classification Search
CPC .... G01N 21/25; G01N 21/251; G01N 21/253; G01N 21/255; G01N 21/256; G01N 21/27; G01N 21/272; G01N 21/274; G01N 21/275; G01N 21/29; G01N 21/293; G01N 21/31; G01N 33/521; G01N 33/523; G01N 33/525; G01N 33/526; G01N 33/528; G01N 21/78
USPC ....... 356/300, 302, 303, 304, 305, 319, 320, 356/326, 328, 402, 405, 406, 407, 408, 356/421, 422, 423, 425
See application file for complete search history.

(56) References Cited

U.S. PATENT DOCUMENTS

| | | | | |
|---|---|---|---|---|
| 3,907,503 | A * | 9/1975 | Betts | G01N 35/00029 422/67 |
| 3,999,047 | A * | 12/1976 | Green | G01N 15/1475 382/134 |
| 5,148,288 | A * | 9/1992 | Hannah | G03B 27/735 356/404 |
| 5,945,341 | A * | 8/1999 | Howard, III | G01N 21/8483 422/566 |
| 6,168,957 | B1 * | 1/2001 | Matzinger | C12Q 1/54 422/422 |
| 6,665,061 | B1 * | 12/2003 | Abou-Saleh | G01N 21/3151 356/318 |
| 7,505,128 | B2 * | 3/2009 | Zribi | G01J 3/02 356/301 |
| 9,241,663 | B2 * | 1/2016 | Jena | G01N 21/8483 |
| 9,311,520 | B2 * | 4/2016 | Burg | G01N 35/00029 |
| 9,778,200 | B2 * | 10/2017 | Tsai | G01N 21/78 |
| 9,911,013 | B2 * | 3/2018 | Davies | C12Q 1/006 |
| 9,990,560 | B2 * | 6/2018 | Decker | G06K 9/4652 |
| 10,267,743 | B2 * | 4/2019 | Burg | G01N 21/78 |
| 2007/0161103 | A1 * | 7/2007 | Buchmann | B26F 1/12 435/287.2 |

(Continued)

*Primary Examiner* — Gordon J Stock, Jr.

(74) *Attorney, Agent, or Firm* — Raymond Y. Chan; David and Raymond Patent Firm

(57) ABSTRACT

The invention provides a test strip comprising an identification region coded a screen function of the test strip by a chromaticity coordinates model; a calibration region having a particular color for calibrating an external spectrum analyzer; and a reaction region chemically reacted with a specific specimen for changing its own color. By using the external spectrum analyzer to conduct light splitting of the reflective lights from the recognition and reaction regions of the test strip, automatic recognition and simplified usage can be achieved.

8 Claims, 5 Drawing Sheets

(56) References Cited

U.S. PATENT DOCUMENTS

| | | | |
|---|---|---|---|
| 2007/0273928 A1* | 11/2007 | Robinson | G01N 33/558 358/3.01 |
| 2008/0267446 A1* | 10/2008 | Capewell | G01N 21/8483 382/100 |
| 2010/0012490 A1* | 1/2010 | Hsu | G01N 21/78 204/400 |
| 2012/0152002 A1* | 6/2012 | Lee | G01N 21/8483 73/61.48 |
| 2012/0189509 A1* | 7/2012 | Hsiao | G01N 21/274 422/400 |
| 2013/0267032 A1* | 10/2013 | Tsai | G01N 21/78 436/95 |
| 2014/0085634 A1* | 3/2014 | Preston | G01J 3/0205 356/327 |
| 2015/0055134 A1* | 2/2015 | Papautsky | G01N 21/25 356/408 |
| 2015/0241358 A1* | 8/2015 | Burg | G01N 21/78 436/164 |
| 2015/0286803 A1* | 10/2015 | Myers | G06T 7/0012 235/375 |
| 2016/0091433 A1* | 3/2016 | Baxi | G01N 21/251 436/23 |
| 2016/0356720 A1* | 12/2016 | Van Dorpe | A61B 5/0066 |
| 2017/0038282 A1* | 2/2017 | Veiseh | G01N 1/10 |
| 2017/0160255 A1* | 6/2017 | Ehlert | G01N 33/182 |

* cited by examiner

600nm

TEST STRIP, INSPECTION SYSTEM AND INSPECTION METHOD THEREOF

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The invention relates to a test strip, more particularly to a test strip that can be analyzed by a spectrum analyzer, and further to an inspection system and method using the test strips.

Description of Related Arts

Screenings, either physical screenings or environmental screenings, become a popular issue as people are getting more aware of self-perceived health status. FIG. 1 is a schematic diagram of a conventional test strip, in which a reaction region 11 is disposed on the conventional test strip 10. When a user puts a specimen on the reaction region 11, a chemical reaction occurs once the specimen encounters the reaction region 11 so as to change a color of the reaction region 11. Therefore, the user can determine whether the specimen is normal or not based on the color change and reference color of the reaction region. Although the conventional test strip 10 can screen, it provides no identifiable marks thereon. If various types of test strips are involved, the user may be easily confused, and the user may use the wrong reference color, which results in an incorrect determination outcome. As a result, the conventional test strip lacks of practicability.

FIG. 2 is a schematic diagram of another conventional test strip, in which an identification region 21 and a reaction region 22 are disposed on the conventional test strip 20. The identification region 21 is a 2D barcode. When the user uses an electronic device (not shown in drawings) to scan the 2D barcode, the user is able to learn the usage of the conventional test strip 20 through the electronic device (not shown in drawings). When the user puts a specimen on the reaction region 22, a chemical reaction occurs once the specimen encounters the reaction region 22, thus, changing the color of the reaction region 22. The user can determine whether the specimen is normal or not based on the color change and reference color of the reaction region 22.

Considering the up-to-date screening technique that is more precise, a spectrum analyzer is generally adopted to determine the amount of color change on the reaction region of the test strip so as to obtain a test result. However, present spectrum analyzers are not only expensive but also limited in their light splitting effects, and they are designed to conduct inspections only for particular wavelength segments. For example, tests for glucose in urine and for hemoglobin (Hb) must be conducted by two spectrum analyzers respectively, and it leads to a high cost. Moreover, regarding the conventional test strip 20 in FIG. 2, not only a spectrum analyzer is needed, but also a 2D barcode scanner is needed to cooperate, which causes inconvenience and is far from practical as well.

SUMMARY OF THE PRESENT INVENTION

One of the purposes of the present invention is to provide a test strip that not only has identification function but also solves effectively the problem of inconvenience as aforementioned.

One embodiment disclosed in the present invention provides a test strip having: an identification region coded a screen function of the test strip by a chromaticity coordinates model; a calibration region having a specific color for calibrating an external spectrum analyzer; and a reaction region chemically reacted with a particular specimen for changing its own color.

Another embodiment of the present invention discloses an inspection system using the test strip, wherein the inspection system comprises: a test strip having an identification region coded a screen function of the test strip by a chromaticity coordinates model; a calibration region having a specific color; and a reaction region chemically reacted with a particular specimen for changing its own color; a spectrum analyzer conducting a light splitting calibration through the calibration region, and generating two light splitting signals based on colors of the identification region and the reaction region; and a display determining a test result according to the two light splitting signals.

The other one embodiment of the present invention discloses an inspection method using the test strip, which comprises the following steps: providing a test strip having an identification region, a calibration region and a reaction region, wherein the identification region is coded a screen function of the test strip by a chromaticity coordinates model; wherein the calibration region has a specific color while the reaction region is chemically reacted with a particular specimen for changing its own color; providing the particular specimen for contacting with the reaction region; providing a light splitting calibration to a spectrum analyzer through the calibration region; splitting reflective lights from the identification region and the reaction region by the spectrum analyzer for generating two light splitting signals; and providing a display for showing a test result which is determined according to the two light splitting signals.

BRIEF DESCRIPTION OF THE DRAWINGS

These and other objects and advantages of the present invention will become apparent from the following description of the accompanying drawings, which disclose several embodiments of the present invention. It is to be understood that the drawings are to be used for purposes of illustration only, and not as a definition of the invention.

DETAILED DESCRIPTION OF THE PREFERRED EMBODIMENT

Although some words has been used in the specification and subsequent claims to refer to particular components, person having ordinary skill in the art will appreciates that manufacturers may use different terms to refer to a component. The specification and claims are not to be differences in the names as a way to distinguish between the components, but with differences in the function of the component as a criterion to distinguish. As mentioned throughout the specification and claims, in which the "include, has, comprise, and with" are an open-ended term, they should be interpreted as "including but not limited to".

Figure 1:
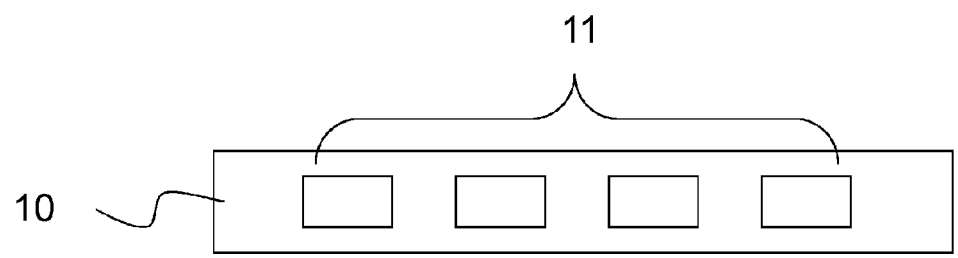
FIG. 1 is a schematic diagram of a conventional test strip
Figure 2:
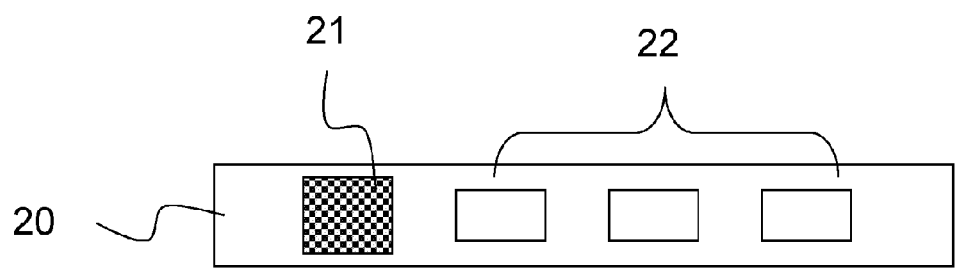
FIG. 2 is a schematic diagram of another one conventional test strip
Figure 3:
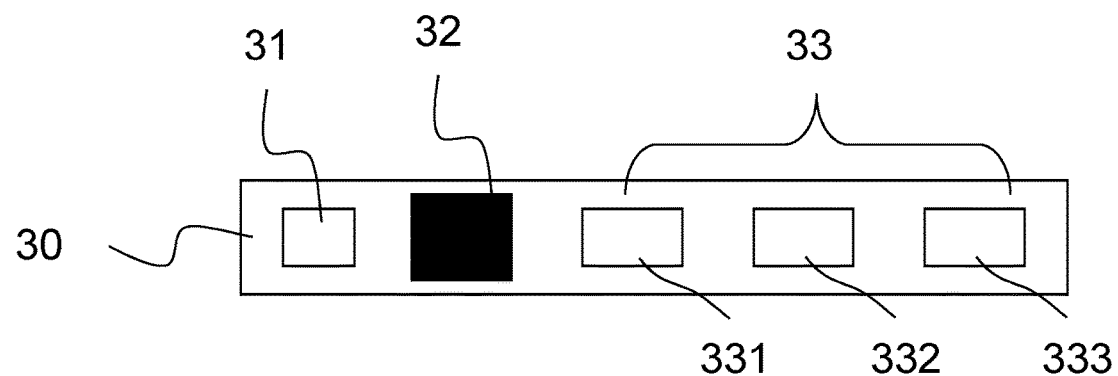
FIG. 3 is a schematic diagram of a test strip disclosed in the present invention

FIG. 3 is a schematic diagram of a test strip disclosed in the present invention, it is shown as: a test strip 30 comprises mainly a calibration region 31, an identification region 32 and a reaction region 33. The calibration region 31 has a specific color, which is generally in white. When an external spectrum analyzer 40 (shown in FIG. 5A) receives a reflective light from the white calibration region 31, it conducts a light splitting and a self-calibration (i.e. light splitting calibration) so as to improve the degree of precision in light splitting. The reaction region 33 is chemically reacted with a particular specimen for changing its own color. Once the external spectrum analyzer 40 (shown in FIG. 5C) receives a reflective light from the reaction region 33, it conducts light splitting and then generates a light splitting signal.

Figure 4:
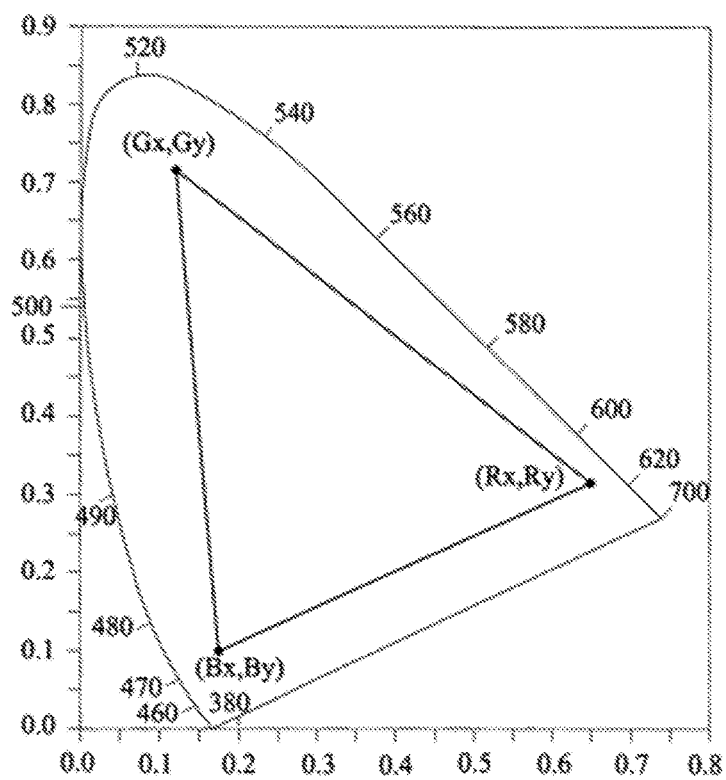
FIG. 4 is a schematic diagram showing a chromaticity coordinates model used by the test strip in the present invention

FIG. 4 is a schematic diagram showing a chromaticity coordinates model used by the test strip in the present invention. As shown in FIG. 4, the x chromaticity coordinate is in presentation of the proportion of primary red, and the y chromaticity coordinate is in presentation of the proportion of primary green. It is obvious to see, from the location of each wavelength shown in the horseshoe-shaped spectrum track, the wavelength section of red spectrum is distributed on the lower right, the wavelength section of the green spectrum is distributed on the upper side, and the wavelength section of the blue spectrum is distributed on the lower left. In addition, the saturation in the center is the lowest while the greatest is found on the light track line. When connecting each dot of wavelength, which represents a different color, on the spectrum track with the central point of the chromaticity diagram, the chromaticity diagram can be divided into various color regions. Therefore, a color characteristic can be defined specifically in the chromaticity by calculating the chromaticity coordinate x and y of a particular color. For example, a cyan sample has a surface chromaticity coordinate of x=0.1902, y=0.2302, and etc. Obviously, different colors have different chromaticity coordinates which allocate at different locations in the chromaticity diagram. Further referring to FIG. 3, the test strip 30 has the identification region 32 that is coded a screen function by a chromaticity coordinate model, which provides coding of the screen functions to different specimens under test. With the advantage of having multiple codes in the chromaticity model, all kinds of test strips can be categorized.

Figure 5A:
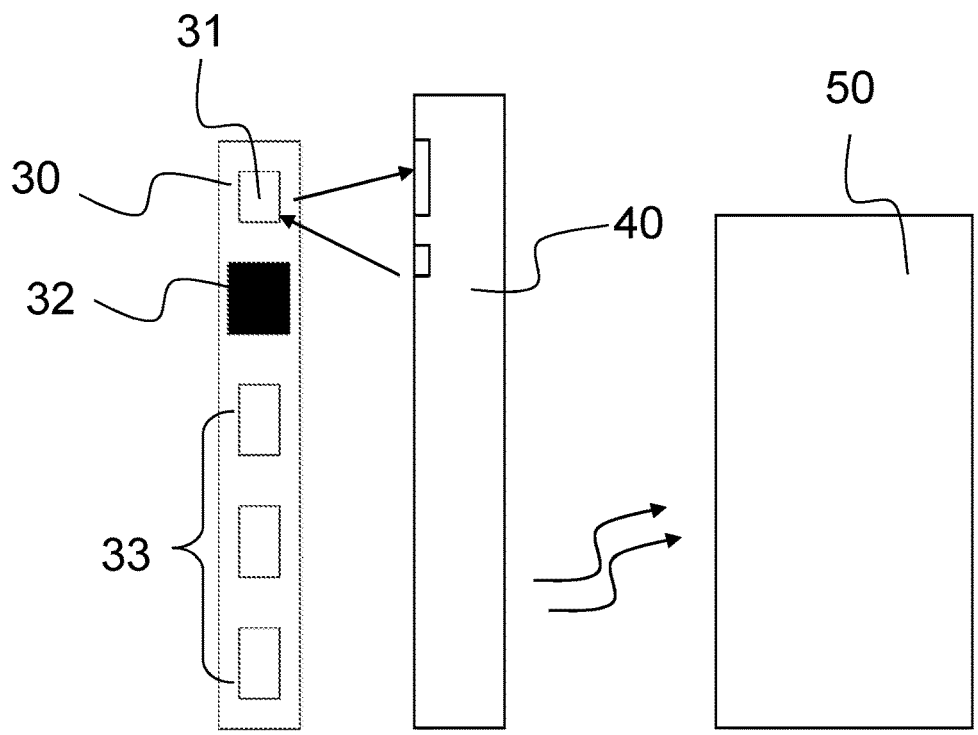
FIGS. 5A through 5C are schematic diagrams showing operations of an inspection system using the test strip disclosed in the present invention
Figure 5B:
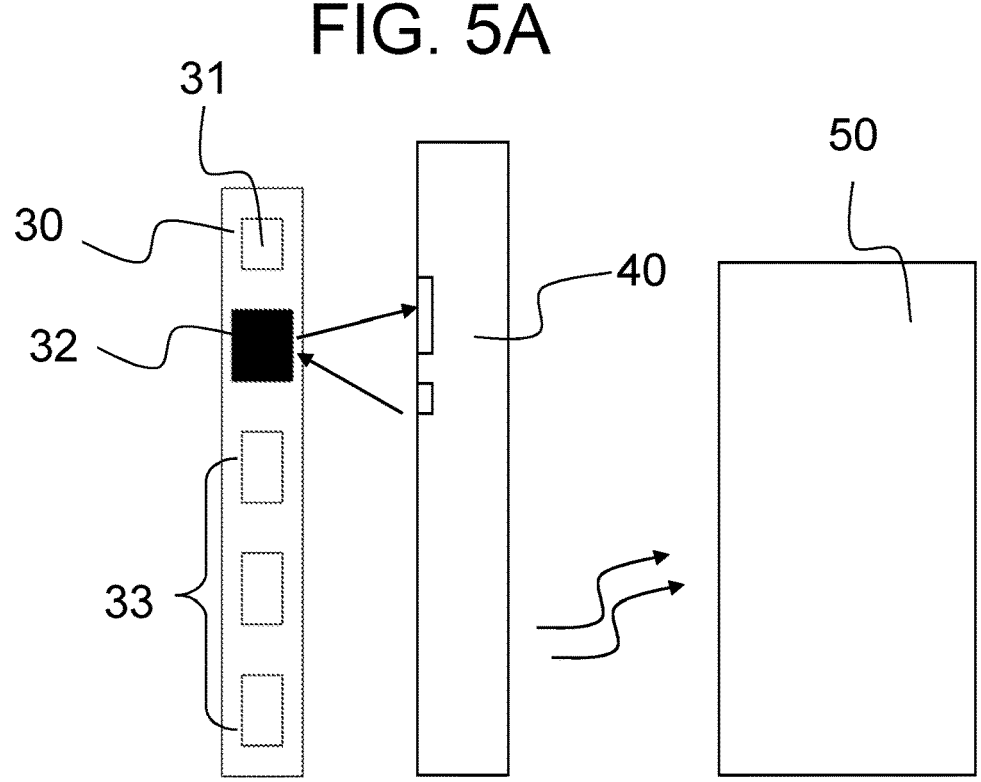
Figure 5C:
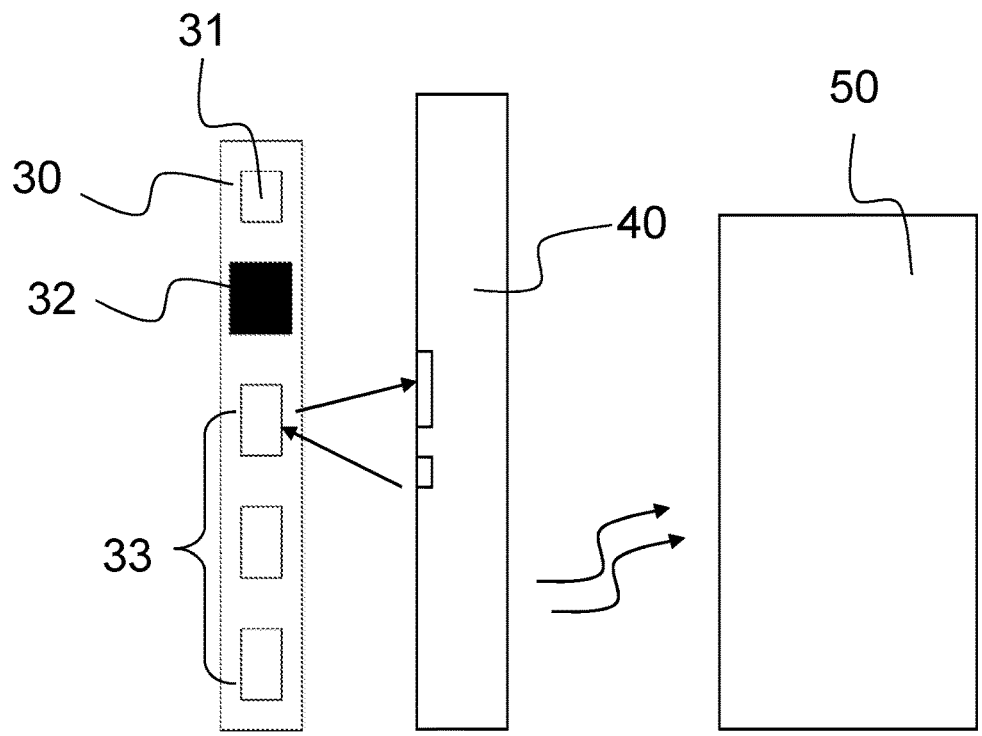

FIGS. 5A through 5C are schematic diagrams showing operations of an inspection system using the test strip disclosed in the present invention, which show: the inspection system using the test strip 30 mainly comprises the test strip 30, a spectrum analyzer 40 and a display 50. The spectrum analyzer 40 conducts a light splitting of the reflective light from the identification region 32 on the test strip 30, and generates one light splitting signal, which is then sent to the display 50. The display 50 determines the category of the specimen under test based on the light splitting signal, and automatically sets up screening parameters. The spectrum analyzer 40 then conducts a light splitting of the reflective light from the reaction region 33 on the test strip 30, and generates another light splitting signal, which is then also sent to the display 50. The display 50 conducts a comparison based on the light splitting signals and the set up screening parameters, and thereby determining the test result for the specimen under test to be normal or otherwise.

Taking a test for glucose value in patient's urine for an example, if the test strip taken is a particular test strip for testing glucose in urine, then a test can be carried out immediately. Assuming that the usage of the test strip is unknown, a user needs to conduct a light splitting calibration on the spectrum analyzer through the calibration region 31 on the test strip 30, once calibration has been completed, the spectrum analyzer 40 receives the reflective light from the identification region 32 of the test strip 30, and transmits the light splitting result either through a physical line or wireless to the display 50, the display 50 then presents the category of the test strip 30, determines the type the specimen under test, and automatically sets up screening parameters according to the light splitting signal. Once the test strip 30 been determined to be used to detect the glucose in urine, the urine under test can be contacted with the reaction region 33 on the test strip 30 (usually is by means of dripping or penetrating). The compositions in the reaction region 33 react chemically with the tested urine for changing the color of the reaction region 33. Additionally, in the reaction region 33, different testing areas 331-333 can be included so that other physical data such as glucose, protein, pH value, occult blood, and etc., can also be tested, which serves a purpose of providing multiple screenings at one test. Once the urine under test is contacted with the reaction region 33 on the test strip 30 for chemical reaction, the test strip 30 can be put into the spectrum analyzer 40. The spectrum analyzer 40 conducts a light splitting calibration based on the reflective light from the calibration region 31 on test strip 30, and also conducts a light splitting of the reflective light from the identification region 32, then transmit light splitting signal to the display 50. The display 50 then presents the category of the specimen under test (glucose in urine) associated with the test strip 30 based on the light splitting signal, and automatically sets up screening parameters related to the glucose in urine. Although the color change in the reaction region 33 may not be visible to humans, the spectrum related to the color change in micro-view is significantly visible after the spectrum analyzer 40 conducts the light splitting. Therefore, the test result is precise relatively.

Figure 6:
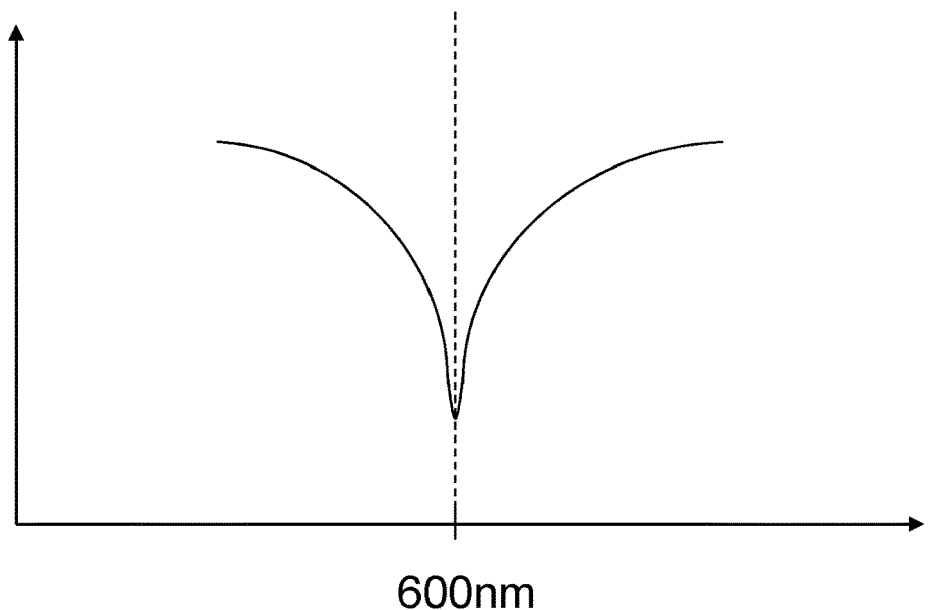
FIG. 6 is a schematic diagram showing a wavelength of a split light disclosed in the present invention

FIG. 6 is a schematic diagram showing a wavelength of a split light disclosed in the present invention. When the test strip 30 is dedicated to test glucose in urine, it is clear to find that reflective light with a wavelength of 600 nm (urinary protein is about 450 nm) from the reaction region 33 has been absorbed after the spectrum analyzer 40 conducts the light splitting of the reflective light, and the degree of absorption, i.e. the magnitude at the valley, represents the value of the glucose in urine. The display 50 compares the degree of light absorption associated with the wavelength at 600 nm and a built-in parameters, and accordingly shows the value of glucose in urine and indicates whether the glucose in urine is normal or not. The user is able to know the test result through the display 50. Therefore, an automatic identification and a simplified yet convenient efficacy can be achieved.

For physiological screenings, the specimen under test can be saliva, urine, blood, stool and etc. For environmental screenings, the specimen under test can be water (for measuring the concentrations of heavy metals), food, poisoned and toxic materials, micro-organisms and so on. Even there are multiple categories, the use of coding the screen function by the chromaticity coordinates model disclosed in the present invention still solves the problem of insufficient category source codes for specimens under test. After the particular composition in each specimen under test is chemically reacted with the reaction region in the test strip, and the light splitting of the reflective light from the reaction region is conducted, the reflective light with the particular wavelength is absorbed. Therefore, the absorbed wavelength parameters can be collected to correspond to specimens under test for forming a parameter truth table, and the parameter truth table is then stored in the display 50 for the use of screening comparison with the light splitting signal.

Figure 7:
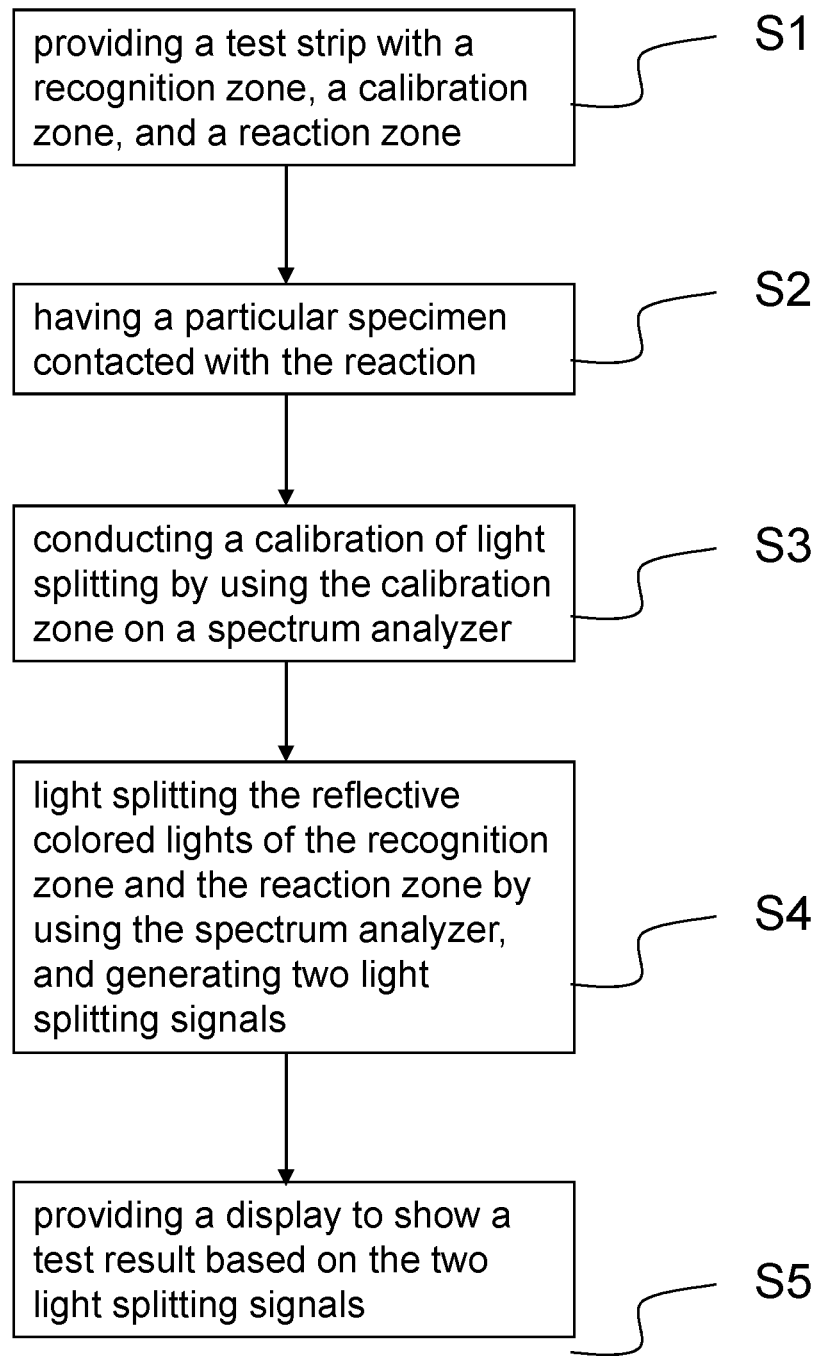
FIG. 7 is a flowchart of an inspection method using the test strip disclosed in the present invention

FIG. 7 is a flowchart of an inspection method using the test strip disclosed in present invention. As shown in FIG. 7, when conducting a test on physiological data, a test strip comprising an identification region, a calibration region and a reaction region needs to be provided first (step S1) so as to react with a specimen under test, wherein the identification region is coded a screen function of the test strip by a chromaticity coordinates model, the calibration region has a specific color, and the reaction region is chemically reacted with a particular specimen, which actually leads to a change in the spectrum (the color of the reaction region is changed if visually viewed by a person); secondly, putting the specimen under test to contact with the reaction region (step S2); then conducting a light splitting calibration of a spectrum analyzer by using the calibration region (step S3) in order to calibrate the spectrum analyzer, wherein execution orders of the S2 and S3 can be exchanged; thirdly, conducting the light splitting of the reflective lights with particular colors from the identification region and the reaction region by using the spectrum analyzer, and accordingly generating two light splitting signals (step S4) to represent the test item and a test result of the test strip, respectively; and finally, providing a display to show the test result based on the two light splitting signals (step S5), which ends the process of the screening.

Additionally, the current spectrum analyzers in the market are not able to conduct a complete analysis on all kinds of light wavelengths, which may be resulted in the imperfect light splitting effect. The reason why the current spectrum analyzers suffering from an imperfect light spitting effect is because the elements inside are not implemented by means of a system-on-a-chip (SOC). Even though a few spectrum analyzers implemented by means of a SOC, the light may be attenuated much after the light is reflected from the rough surface, such that analysis is beyond possible. Hence, the spectrum analyzer 40 in the present invention is implemented by means of SOC, and elements inside (reflective light reception part and grating) the SOC are completed by utilizing a high energy light source with wavelengths ranged between 0.01 nm and 100 nm to expose a photoresist layer, and then removing the unexposed photoresist layer. By so doing, not only the size of the spectrum analyzer 40 can be reduced, but also the surface roughness can be decreased, thereby enabling the reflective light to be almost fully reflected without attenuation, which achieves the effect of a complete light splitting.

There have thus been shown and described an improved test strip, an inspection system and a method using the test strip. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention.

What is claimed is:

1. A test strip, comprising:
an identification region, coded a screening function of the test strip by a chromaticity coordinates model which comprises a first chromaticity coordinate which is in presentation of a proportion of a first color and a second chromaticity coordinate which is in presentation of a proportion of a second color to enable different colors having different chromaticity coordinates which allocate at different locations in a chromaticity diagram;
a calibration region, having a particular color for calibrating an external spectrum analyzer; and
a reaction region, chemically reacted with a particular specimen for changing its own color.

2. An inspection system of test strips, comprising:
a test strip comprising:
an identification region, coded a screening function of the test strip by a chromaticity coordinates model which comprises a first chromaticity coordinate which is in presentation of a proportion of a first color and a second chromaticity coordinate which is in presentation of a proportion of a second color;
a calibration region, having a particular color; and
a reaction region, chemically reacted with a particular specimen for changing its own color;
a spectrum analyzer, conducting a light splitting calibration through the calibration region, simultaneously receiving reflected lights with particular colors from both of the identification region and the reaction region, conducting light splitting of the reflected lights with the particular colors, and generating two light splitting signals based on colors of the identification region and the reaction region; and
a display, determining a test result according to the two light splitting signals.

3. The inspection system of test strips of claim 2, wherein the spectrum analyzer is a system-on-a-chip (SOC), and elements inside the SOC are completed by utilizing a high energy light source with wavelengths ranged between 0.01 nm and 100 nm to expose a photoresist layer, and then removing the unexposed photoresist layer.

4. An inspection system of test strips, comprising:
a test strip comprising:
an identification region, coded a screening function of the test strip by a chromaticity coordinates model;
a calibration region, having a particular color; and
a reaction region, chemically reacted with a particular specimen for changing its own color;
a spectrum analyzer, conducting a light splitting calibration through the calibration region, and generating two light splitting signals based on colors of the identification region and the reaction region; and
a display, determining a test result according to the two light splitting signals, wherein a parameter truth table is stored in the display, and the test result is generated by comparing the two light splitting signals with the parameter truth table.

5. An inspection method of test strips, including the following steps:
   providing a test strip comprising an identification region, a calibration region and a reaction region; wherein the identification region is coded a screening function of the test strip by a chromaticity coordinates model which comprises a first chromaticity coordinate which is in presentation of a proportion of a first color and a second chromaticity coordinate which is in presentation of a proportion of a second color;
   wherein the calibration region has a particular color; and wherein the reaction region is chemically reacted with a specific specimen for changing its own color;
   providing the specific specimen for contacting with the reaction region;
   providing a light splitting calibration to a spectrum analyzer through the calibration region;
   simultaneously receiving reflected lights with particular colors from both of the identification region and the reaction region, conducting light splitting of the reflected lights with the particular colors, and splitting reflective lights from the identification region and the reaction region by the spectrum analyzer for generating two light splitting signals; and
   providing a display for showing a test result which is determined according to the two light splitting signals.

6. The inspection method of test strip of claim 5, wherein the specific color is white.

7. The inspection method of test strips of claim 5, wherein the spectrum analyzer is a system-on-a-chip (SOC), and elements inside the SOC are completed by utilizing a high energy light source with wavelengths ranged between 0.01 nm and 100 nm to expose a photoresist layer, and then removing the unexposed photoresist layer.

8. An inspection method of test strips, including the following steps:
   providing a test strip comprising an identification region, a calibration region and a reaction region; wherein the identification region is coded a screening function of the test strip by a chromaticity coordinates model; wherein the calibration region has a particular color; and wherein the reaction region is chemically reacted with a specific specimen for changing its own color;
   providing the specific specimen for contacting with the reaction region;
   providing a light splitting calibration to a spectrum analyzer through the calibration region;
   splitting reflective lights from the identification region and the reaction region by the spectrum analyzer for generating two light splitting signals;
   providing a display for showing a test result which is determined according to the two light splitting signals; and
   storing a parameter truth table inside the display, thereby the test result is generated by comparing the two light splitting signals with the parameter truth table.

* * * * *